United States Patent [19]

Kratochwilla

[11] Patent Number: 4,801,265
[45] Date of Patent: Jan. 31, 1989

[54] CONTROL VALVE DEVICE FOR A DENTAL DEVICE

[75] Inventor: Hans-Michael Kratochwilla, Lorsch, Fed. Rep. of Germany

[73] Assignee: Siemens Aktiengesellschaft, Berlin and Munich, Fed. Rep. of Germany

[21] Appl. No.: 89,948

[22] Filed: Aug. 26, 1987

Related U.S. Application Data

[63] Continuation of Ser. No. 796,712, Nov. 12, 1985, abandoned.

[30] Foreign Application Priority Data

Nov. 23, 1984 [DE] Fed. Rep. of Germany ....... 3442846

[51] Int. Cl.$^4$ ............................................ F16K 11/065
[52] U.S. Cl. ..................................... 433/98; 137/595; 137/597; 137/625.18; 137/883; 251/327; 251/368
[58] Field of Search ................... 137/625.33, 883, 885, 137/595, 625.18, 597, 594; 251/327, 363, 368; 285/364, 396, 128, 129; 433/98

[56] References Cited

U.S. PATENT DOCUMENTS

| | | | |
|---|---|---|---|
| 2,576,848 | 11/1951 | Mercier et al. | 137/625.33 |
| 2,986,367 | 5/1961 | Le Rouax | 251/327 X |
| 2,993,488 | 7/1961 | Stec | 137/625.33 X |
| 3,479,069 | 11/1969 | Sedan | 285/364 |
| 3,494,377 | 2/1970 | Thuse | 137/625.18 |
| 3,545,906 | 12/1970 | Meneret et al. | 137/625.18 X |
| 3,614,061 | 10/1971 | Fitzpatrick | 251/327 |
| 3,621,878 | 11/1971 | Smith | 137/595 |
| 3,918,161 | 11/1975 | Morgan et al. | 433/27 |
| 3,918,489 | 11/1975 | Foster et al. | 137/883 X |
| 4,136,450 | 1/1979 | Güenther et al. | 433/27 |
| 4,145,813 | 3/1979 | Hall | 137/625.18 X |
| 4,241,761 | 12/1980 | Miller | 137/883 |
| 4,352,511 | 10/1982 | Ribble et al. | 285/364 X |
| 4,489,756 | 12/1984 | Balz | 137/625.33 |
| 4,493,476 | 1/1985 | Strickland | 251/327 |

FOREIGN PATENT DOCUMENTS 1392349 4/1975 United Kingdom ................ 251/327

Primary Examiner—Martin P. Schwadron
Assistant Examiner—Stephen M. Hepperle
Attorney, Agent, or Firm—Hill, Van Santen, Steadman & Simpson

[57] ABSTRACT

The present invention is directed to a control valve device or arrangement for the simultaneous control of a plurality of fluid agents in a dental device. The control valve device arrangement comprises a valve member and a housing member composed of at least one part. Preferably, the housing member and the valve member are plate-like members which are arranged in a sandwich-like fashion with the valve member interposed between the two plates of the housing member and an arrangement is provided for shifting the valve member relative to the plates of the housing member. Each of the plates forming the valve member and the housing member are composed at least along the sliding surfaces of a ceramic material which is super-fine or smooth to form a sealing relationship therebetween. In the preferred embodiment, each of the three plate-like members are composed of the ceramic material and the valve member has through-passages which are arranged in the pattern which is the same as the pattern of ports provided in each of the plate members so that as the valve member can be shifted from a position with the through-passages out of alignment with the ports to block the flow of the agent to another position with the opening of the bores aligned with the pattern of openings or ports to permit flow of all of the agents simultaneously.

17 Claims, 4 Drawing Sheets

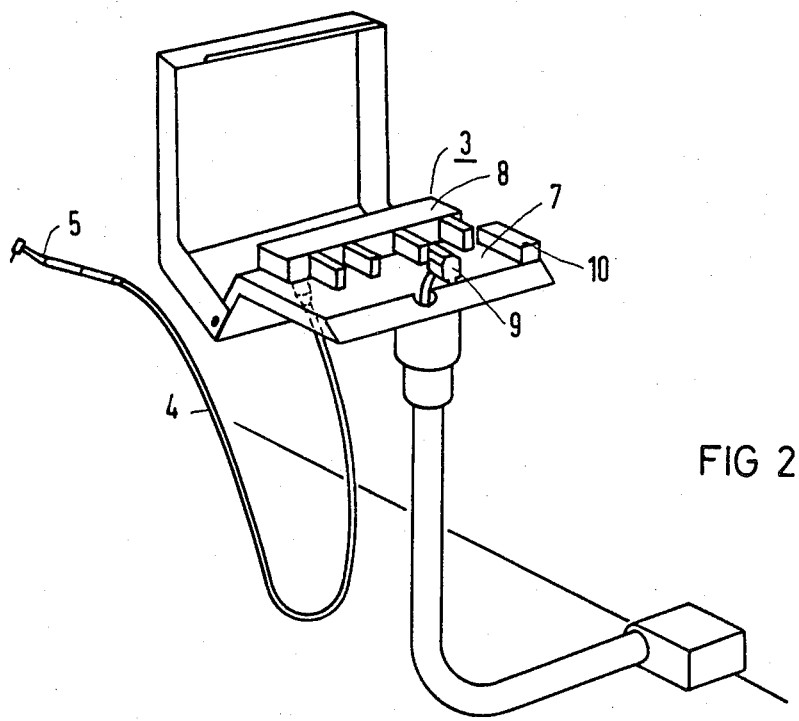
FIG 2
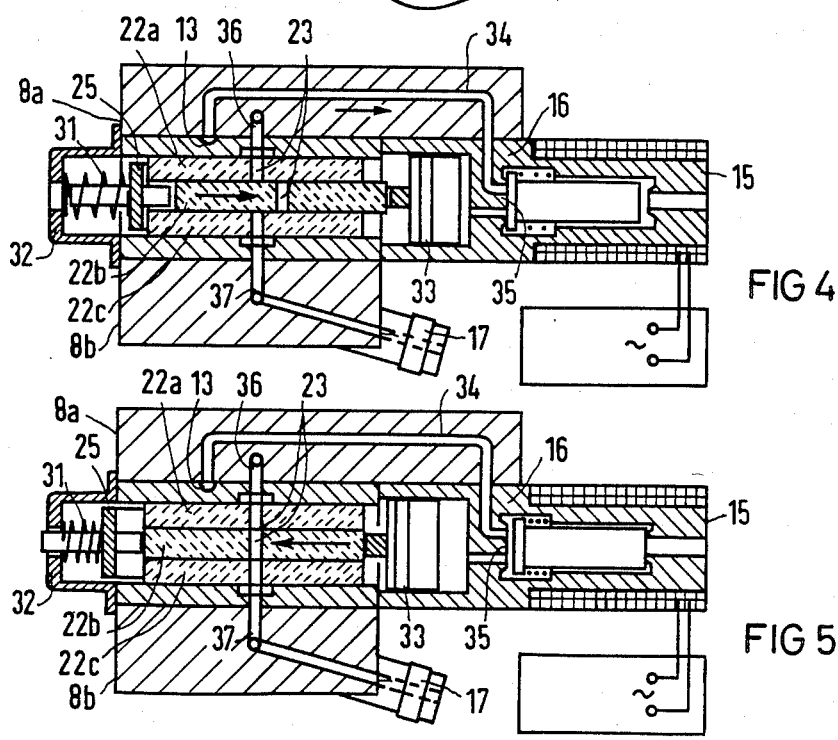
FIG 4
FIG 5

CONTROL VALVE DEVICE FOR A DENTAL DEVICE

This is a continuation of application Ser. No. 796,712, filed Nov. 12, 1985, now abandoned.

BACKGROUND OF THE INVENTION

The present invention is directed to control valve means for a dental service.

Tappet valves or diaphragm valves have been utilized in medical, particularly dental devices, for the control of the flow of agents such as air, water and mixtures thereof. When a diaphragm valve is utilized, a diaphragm is clamped between two valve body parts and the diaphragm is then charged on one side with a control agent, for example, air, so that it closes two openings on the other side of the diaphragm. One of these openings extends to an agent feed line and the other to a discharge line. Thus, with the diaphragm closing these openings, flow between the input or feed line to the discharge line is prevented and when the control agent is released, the diaphragm will move to uncover the two openings to allow flow between the input and discharge lines. Examples of such control valves are disclosed in U.S. Pat. No. 3,918,161 and U.S. Pat. No. 4,136,450 whose disclosures are incorporated by reference thereto.

Diaphragm valves of the above-mentioned type are relatively susceptible to sticking as well as to deposits on or in the valve seat area so that the required tightness at the closed valve can very quickly disappear under given conditions. Thus, the operational reliability of the control valve means will deteriorate. This is also true of the former tappet valves or, respectively, of a combined diaphragm and tappet valves, particularly given their use for controlling aqueous agents because the particular dangers exist that the parts of the valves such as the tappet, compression springs, etc. will lead to a premature failure of the control valve means because of corrosion of these parts.

SUMMARY OF THE INVENTION

The present invention is directed to a control valve means or device for a dental service which has a control valve among other things in which the aforementioned disadvantages can be avoided and which, in particular, is operationally reliable and over and above this, functions independent of position. The latter is of significance, for example, when a valve is integrated into a movable device, for example, into a hand instrument or the like where no particular consideration can be taken with instruct to the specific built-in position.

Essential advantages of the control valve means or device of the invention are that separate paths for a plurality of agents can be controlled via one valve arrangement in a simple and reliable way. The valve bodies fashioned of a ceramic material preferably of aluminum oxide ceramic (96% $Al_2O_3$) are excellently resistant to corrosion, have no chemical affinity to the agent flowing through the conduit paths and do not tend toward sticking or being contaminated. Due to the relative motion of the valve member and the base member which can be fashioned as a longitudinal motion or a turning motion, a good self-cleaning effect is established among other things.

It is particularly advantageous to fashion the valves as flat slide valves wherein each valve is composed of a packet of three superimposed plates of ceramic material of which the upper and lower plates are arranged and held stationary and the middle plate is mounted in a frame which is adjustable by means of a suitable adjustment means which can be either of a manual means or of a pneumatic, hydraulic or electromechanical type. The sealing between the plates occurs due to the superfine sliding surfaces. All of the plates advantageously have the same pattern for holes or apertures so that every valve can simultaneously open and close up to five channels.

It is particularly advantageous to provide such a flat slide valve for the control of the flow of agents for a plurality of dental instruments whereby it can be advantageous for their use to arrange the valves in a shared valve block housing and to provide a common input slide valve for all instruments for this purpose and a respective output slide valve for each instrument. The valves are advantageously accommodated in the valve block housing constructed sandwich-like which is essentially composed of two housing parts, an upper valve block housing in which the agent feed and conduits for the distribution of the agents to the individual valves are situated and a lower valve block part which contains the conduits leading away from the valves and the connection fittings for the supply hoses leading to the individual instruments.

Further embodiments and advantages of the invention will be readily apparent from the following description of the preferred embodiments.

BRIEF DESCRIPTION OF THE DRAWINGS

FIG. 2 is a rear perspective view of the dental device of FIG. 1;

FIG. 4 is a longitudinal cross-sectional view of a control valve means in accordance with the present invention with the valve in a shut-off position;

FIG. 5 is a longitudinal cross-sectional view similar to FIG. 4 with the valve of the control valve means in an open position.

DESCRIPTION OF THE PREFERRED EMBODIMENT

Figure 1:
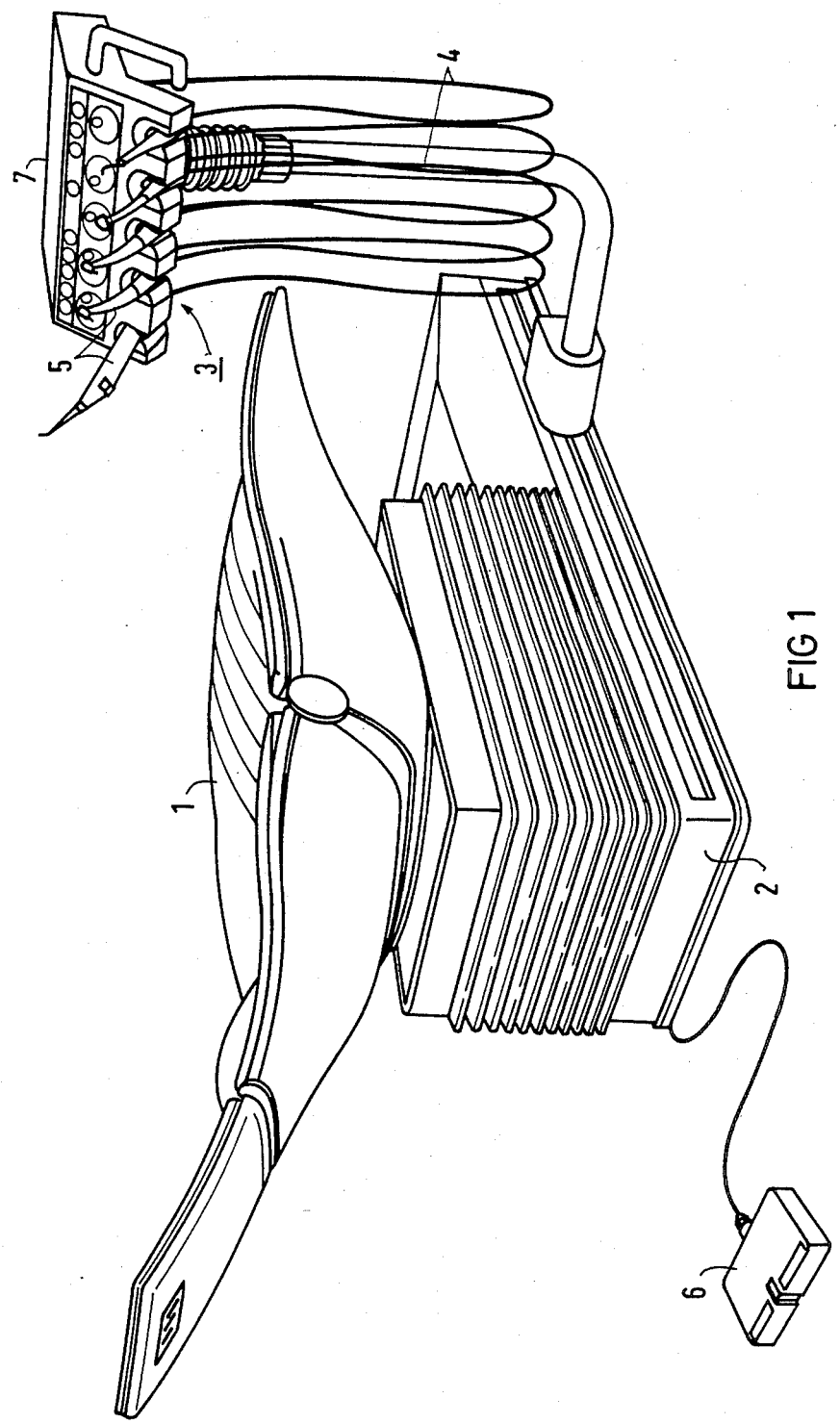
FIG. 1 is a perspective view of a dental work station having the dental device in accordance with the present invention.

The principles of the present invention are particularly useful when incorporated in a dental work station of FIG. 1 which contains a dental patient chair 1 having a chair base 2 and a medical device which is longitudinally displaceable along the base 2 and is generally indicated at 3. The medical device 3 has a housing 7, which has storage positions or deposit positions for receiving instruments 5. Each of the instruments 5 is connected to a hose or supply line 4 to the housing 7 of the medical device. As illustrated, the dental work station also includes a foot switch 6, which controls the operation of each of the various instruments 5. For example, the switch may control the actuation of the drives for the handpieces such as either an air motor or an electric motor or in the instance of spray devices, the foot switch can control the connection and disconnection of cooling agents which are to be discharged through the spray device.

As best illustrated in FIG. 2, the medical device 3 has its housing opened. In the interior of the housing are a control valve block 8, a coupling member 9 and an electrical heating means 10 with which the agents can be heated as needed in a known way.

Figure 3:
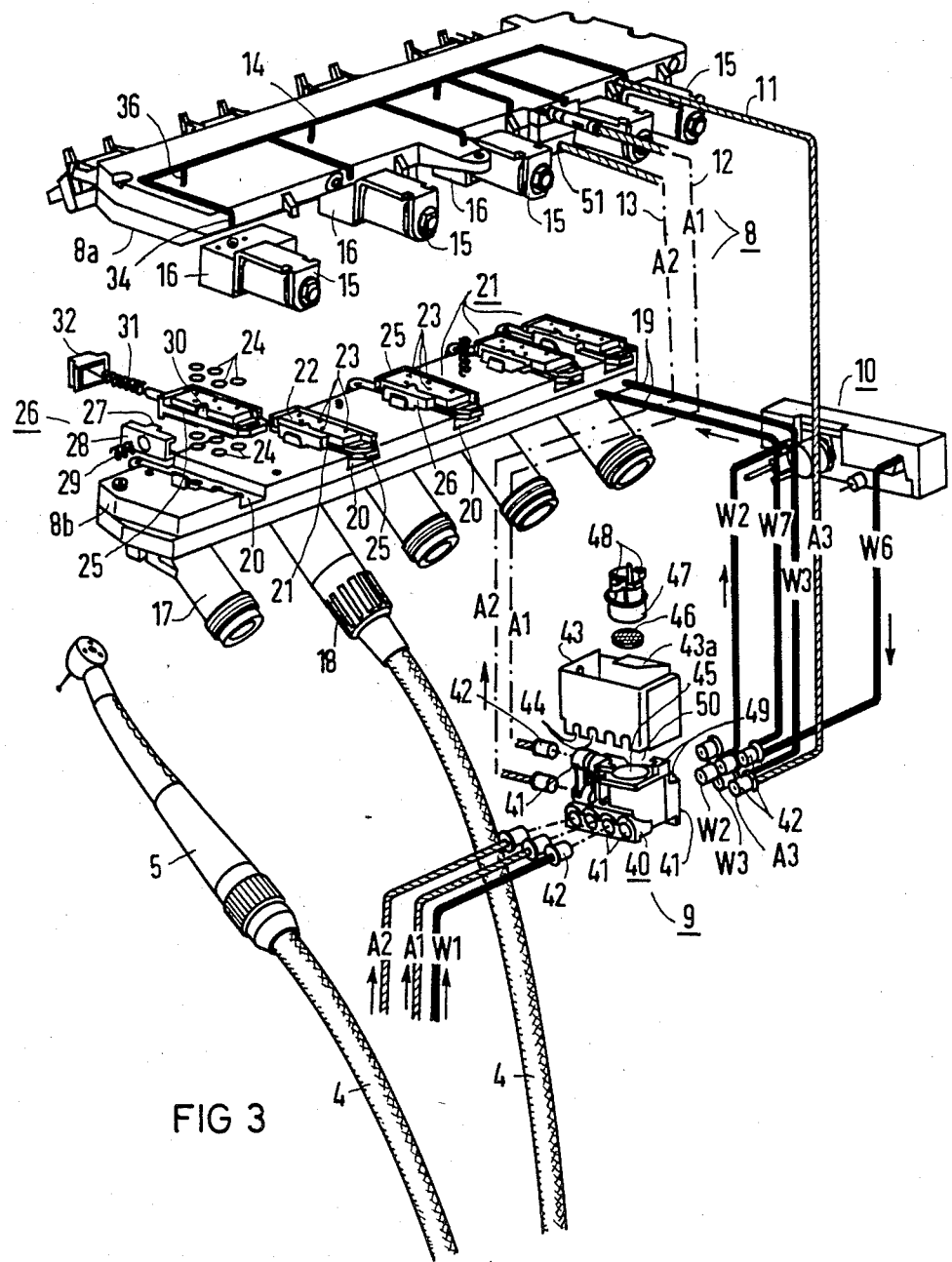
FIG. 3 is an exploded perspective view of a valve control means for the dental device of the present invention.

The control valve block 8, the coupling member 9 and the heating member 10 are illustrated in FIG. 3 in an exploded view of the structure so that the parts essential to the invention can be easily perceived. The agent flow is indicated with solid lines in the illustration for water and with shaded lines for air and these lines are further identified by the abbreviations W for water and A for air.

The control valve block 8 is essentially composed of two housing parts, which are respectively formed of two plates and include an upper housing part or plate 8a and a lower housing part or plate 8b. Feed lines 11, 12 and 13 are connected into the upper part 8a. As illustrated, these feed lines can be a chip blower air line 11, a drive air line 12 and a control air line 13. Distribution of the agent supplied via the lines such as 11 and 12 to the various valve positions shall be described in greater detail below and occurs via channels and bores such as 14 which have been formed in the plates in a known way or have been formed to extend through the various plates. The control valve block 8 is illustrated as having five valve stations. Valves 15 which are solenoid valves are connected to the upper housing part 8a and are respectively coupled to pneumatic control means 16. The lower housing part 8b contains a connecting sleeve or member 17 for connection of hose fittings 18 of the supply line 4 for each of the instruments 5 and also contain connections 19 for water lines W3 and W7 which are cold spray water and a warm spray water lines. On an upper surface of the lower housing part 8b, five grooves 20, which extend at right angles to the relatively longitudinal extent of the housing part 8b are provided. Valves 21 are arranged in these grooves 20. A corresponding groove is also formed on the undersurface of the upper housing part 8a and coact with the grooves 20 to totally receive the valves 21 with the undersurfaces lying flush against one another in the assembled condition of the two housing parts 8a and 8b.

In the illustrated embodiment, the valves 21 are slide valves. Each slide valve is composed of a packet of three ceramic plates, members or disks 22a, 22b and 22c (see FIGS. 4 and 5) which are arranged on top of one another which in the exemplary embodiment are fashioned as relatively thin plates having a rectangular cross-section and configuration. Each of these three ceramic members 22a, 22b and 22c contains five through-bores 23 which are arranged offset but at the same location so that every plate has the same pattern for the holes or bores. The individual bores 23 of the plates 22a and 22c are sealed from one another upon interposition of sealing rings 24 (FIG. 3). The sealing rings are provided only between the upper ceramic member 22a and the plane surface of the groove in the upper housing part 8a and between the lower ceramic member 22c and the plane surface of the groove 20 of the lower housing part 8b. The sealing between the ceramic members 22a, 22b and 22c occurs only on the basis of the super-fine slide surfaces of these parts. The sealing rings are selected to be slightly thicker than the clearance provided for their mounting so that the members are arranged "floating" between the housing parts.

In addition to their sealing functions, the sealing rings thus also fulfill the job of exerting a certain biasing force against the slide surfaces of the disks or plates 22a, 22b and 22c. As illustrated in FIGS. 4 and 5, the surface of the groove in the parts 8a and 8b can be provided with counterbores to provide the mounting for each of the sealing rings adjacent the port formed in the part.

The middle ceramic disk or plate 22b is mounted in a frame 25 as best illustrated in FIGS. 4 and 5. As best illustrated in FIG. 3, the upper and lower ceramic plates 22a and 22c are rigidly fixed in the valve control block housing 8 by means of a holding device 26. As may be seen from this, the holding means or device 26 is composed of a U-shaped retaining part 28 which has a catch nose 27 on each of its two legs which catches noses are received in notches 30 in the upper and lower ceramic plates 22a and 22c. A spring 29 is provided to urge the retaining part 28 so that the noses 27 are urged into the notches 30. As a consequence of this arrangement, the two outer ceramic plates 22a and 22c are held fast in the housing during movement of the middle plate.

The frame 25 for the middle plate 22b (see FIGS. 4 and 5, is pressed against a detent in the direction of its longitudinal axis by means of a compression spring 31 which is supported against a cap 32 which can be fixed in the valve control block 8. The detent is formed by a piston 33 of a pneumatic control means 16 which can be charged with compressed air via a solenoid valve 15. As illustrated in FIG. 4, the piston 33 is in a retracted position and the slide 22b is in a second position with the bores of the plate 22b out of alignment with the ports in the plates 22a and 22c. The slide can be moved to a first position illustrated in FIG. 5 wherein its bores are aligned with the bores in the stationary members 22a and 22c.

When the instrument is not in use, the middle ceramic plate 22b resides in the second position of FIG. 4 due to being pushed there by the spring 31. The piston 33 is situated in its retracted position. In this position, the pattern for the holes of the middle ceramic plate 22b is not congruent with the pattern for the holes which form the ports for the upper and lower plates 22a and 22c. In this position, the flow of an agent via the five bores (only one is visible in FIGS. 4 and 5) is blocked and thus the valves 21 prevents flow of any of the agents.

When the solenoid valves 15 receives an operating voltage, for example, when an instrument 5 is removed from its deposit, then the solenoid will uncover a sealing face 35 to allow compressed air from a compressed air line 34 to act against the piston 33. The piston will then shift to the left as illustrated in FIGS. 4 and 5 move the plate 22b to the first position illustrated in FIG. 4 which will cause the bore pattern of the middle ceramic disk 22 to become aligned with the bore pattern in the outer plates 22a and 22b. In this position which is illustrated in FIG. 5, a flow of the agents through the valve is established. For example, a feed channel 36 which is in the upper housing part 8a and is connected to one of the feed lines 11 or 12 will be connected through the aligned bores 23 to discharge channel 37 in the lower housing part 8b which is connected to the supply line 4 of the instrument associated with that particular valve.

The compressed air needed for the control of the piston 33 is adjacent to all pneumatic control devices 16 simultaneously via lines 13, 14 and 34. An invididual release only occurs via an electrical control signal to the solenoid valve 15. This signal can be generated via the foot switch 6 or when one of the instruments is removed from its deposit or storage position.

The functioning of the coupling member 9 is discussed hereinbelow. The coupling member 9 promotes the service friendliness of the overall control valve means and particularly the connected function modules can be easily separated without the assistance of tools. The coupling member 9 (FIG. 3) contains a molded part such as a base body 40 comprising a plurality of respectively identical bores 41 for receiving plug-type connecting nipples 42. These plug-type connecting nipples 42 which are connected to the intake and discharge lines for air and water can be connected to the base body 40 of the coupling member 9 either individually or joined in a plurality on a common strip. An interlock capsule 43 is provided and slips over the base body 40 after the plug-type connecting nipples 42 have been inserted into the corresponding bores 41. As illustrated, the capsule 43 has a plurality of fork-like notches 44 which engage the nipples while in their plugged-in position as the capsule 43 is slipped on the base body to either lock or fix the connecting nipples 42 in their respective bores 41.

The base body 40 also contains a central bore 45 for the acceptance of a filter 46 and of a filter carrier 47. The filter carrier 47 contains an interlock nose 48 which engages into a correspondingly fashioned cooperating member 49 on the base body 44 when the filter carrier is inserted in the bore and is turned to form a bayonet-like connection. In this position, a tab 43a on the interlock capsule 43 lies in a recess 50 of the base body 40 and is held there by the filter carrier 47 as a consequence of the bayonet connection formed by the parts 48 and 49. As a result of the bayonet-like closure, all plug-type connecting nipples can be removed after the filter carrier has been removed and after the interlock capsule has been subsequently pulled off of the base body and thus the attached function modules can be separated from one another.

Figure 6:
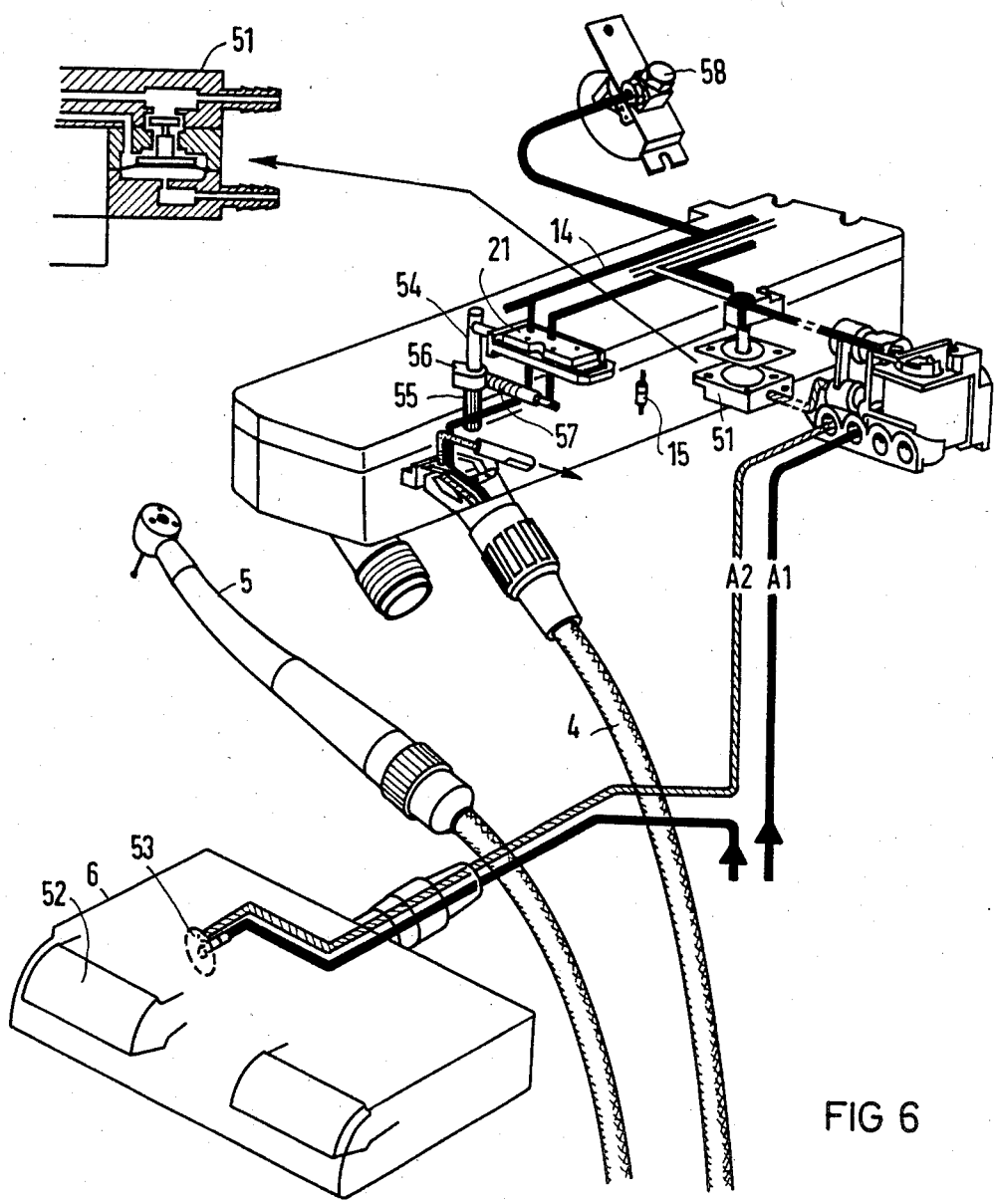
FIG. 6 is a perspective view schematically illustrating the agent course for one instrument in accordance with the present invention.

The path of the drive air for the turbine handpiece or instrument can be explained in greater detail with reference to FIG. 6. Compressed air is introduced by a line A1 to a pneumatic valve 51 which is located in the lower valve block housing 8b and normally closed. When the pneumatic valve 51 is opened, the compressed air will enter into the branching system 14 in the upper valve block housing 8a and be adjacent each of the valves 21. As soon as the instrument 5 is taken from its deposit, the electrical signal that is created will actuate the solenoid valve 15 and as explained hereinabove, causes control air via line 34 to act on the piston 33 associated with that particular valve to cause the middle plate or member 22b to move from the closed position to a position interconnecting the ports in the upper valve member with the ports in the lower valve member. By depressing a foot pedal 52, another valve 53 coupled to it is opened so that control air will enter line A2 and is applied to the diaphragm valve 51 to cause it to open. The drive air now flows into the supply hose 4 for that particular instrument. Shortly before the air enters the hose 4, the air will also pass through a pressure regulator valve 54 which has a control knob 55 on the underside of the valve block housing 8b to shift a valve member 57 via an eccentric 56. Thus, the pressure of the drive air can be set to a prescribed valve which will be indicated on a common pressure manometer 58.

The control of other agents such as chip blower air and spray water will occur in a similar fashion.

It may be seen from the illustrations that the overall valve control block contains a very compact path and valve system with which the unnecessary line connections and line paths which necessarily lead to pressure losses and also contain the risk of leaks are reduced to a minimum. The valve block contains pratically only connections for the feed of water and air as well as control means (pressure regulator, valve, distributor channel) for the distribution of the agents to the respective instruments. The separately arranged central coupling member 9 allows a fast connection and removal of the feed and discharge lines and thus enables a quick replacement of components. In that the supply hoses 4 are directly connectible to connecting elements of the distributor block, the connecting lines to the respective valves which are otherwise necessary are likewise eliminated. The drive air for the instruments driven with compressed air is not conducted through the foot switch but in the present arrangement, a pneumatic signal is merely formed in the foot switch and this is amplified in the control valve block to control the flow of the compressed air for driving an air motor. Thus, different lengths of the foot switch cable and different apparatus adaptations do not have a disadvantageous effect on the flow quantities required for the air-driven instrument.

It should be noted that in the above disclosure, a longitudinal motion of the ceramic plate or member is described. However, this is not required. It is conceivable and within the framework of the present invention for the ceramic disk to be rotated relative to one another and their hole pattern to be brought into coincidence upon rotation. Instead of utilizing plate-shaped planar disks, it is also conceivable to provide curved surfaces, for example, a cylindrical valve member or a spherical valve member of ceramic material which interact with correspondingly fashioned cooperating surfaces in the described way so that a seal between the ceramic parts is also established solely by the sliding ceramic surfaces which are super-fine or smooth. The use is not limited to the described valve block. Thus, as a result of extremely small dimensions with which the ceramic slide valves need, a direct integration into a foot switch or even into a dental handpiece is also conceivable.

Although various minor modifications may be suggested by those versed in the art, it should be understood that I wish to embody within the scope of the patent granted hereon, all such modifications as reasonably and properly come within the scope of my contribution to the art.

I claim:

1. In a control valve means for a dental device for the simultaneous control of a plurality of fluid agents, said control valve means containing at least one valve, which is composed of a plurality of parts arranged on top of one another sandwich-like and forming the valve seat therebetween, an intake and discharge line for each of the plurality of agents as well as control lines under given conditions being connected to the valve, the improvements comprising said control valve means having a single valve control block having an output control valve for each instrument associated with the valve means and a common input control valve, each of said output control valves containing two stationary spaced plates with one plate having ports being connected to the agent intake lines and the other plate having ports being connected to the discharge lines, and a movable plate forming a valve body adjustably arranged between the two stationary plates and having through-channels proceeding at right angles to a plane of movement, said plates comprising super-fine sliding surfaces of ceramic material with which the plates lie against one another, and adjustment means including a solenoid valve and associate pneumatic control means for moving said movable plate along said sliding surfaces of the stationary plates between at least two positions with one of the two positions having the through-channels of the movable plate being aligned with the ports formed in the two stationary plates to enable flow therebetween and a second of the two positions having the through-channels of the movable plate out of alignment with the ports of the stationary plates to block flow of the agents, said valve control block having an upper part and a lower part, said upper part having connections for the feed the agents to each of said output control valves, and said lower port having a hose connection for each of the output control valves for connecting a supply conduit thereto.

2. In a control valve means according to claim 1, wherein the ports in the stationary plates facing the movable plate and the through-channels of the movable plate have the same hole pattern.

3. In a control valves means according to claim 2, wherein the movable plate and the two stationary plates are fashioned in identical form.

4. In a control valve means according to claim 3, wherein the movable plate and the stationary plates are completely composed of ceramic material.

5. In a control valves means according to claim 4, wherein the movable plate and the stationary plates are each flat lamina having an essentially rectangular configuration, the movable plate being arranged to be movable in a direction of its longitudinal axis.

6. In a control valve means according to claim 5, wherein the lamina forming the movable plate is mounted in a frame which is held in the second position by a spring means and is brought into the one position by a dislocating means acting opposite to each direction of said spring means, wherein the agent flow through the middle lamina is established in said one position and is blocked when the lamina is in said second position.

7. In a control valve means according to claim 6, wherein the dislocating means include a piston and means for applying air against said piston to move it between a retracted and second position.

8. In a control valve means according to claim 1, which includes a common coupling member being present for the various agents, said common coupling member having bores for receiving plug-type connecting nipples of the various agents and having an interlock capsule having means to interlock the connecting nipples in their plug-in position when the capsule is slipped onto the coupling member.

9. In a control valve means according to claim 8, wherein the coupling member contains a filter carrier which contains interlocking elements which can be brought into engagement bayonet-like with cooperating elements of the coupling member, said interlock capsule being held in the plug-in position by means of this interlock element.

10. In a control valve means for a dental device for the simultaneous control of a plurality of fluid agents, said control valve means containing at least one valve, which is composed of a plurality of parts arranged on top of one another sandwich-like and forming a valve seat therebetween, an intake and discharge line for each of the plurality of agents as well as control lines under given conditions being connected to the valve, the improvements comprising the valve containing two stationary spaced plates with one plate having a plurality of ports with each port connected to a separate agent intake line and the other plate having a plurality of ports with each port being connected to a separate discharge line, and movable plate forming a valve body adjustably arranged between the two stationary plates and having a through-channel proceeding at right angles to a plane of movement of the plate for each port in the one plate, each of said plates comprising a flat lamina completely composed of a ceramic material to provide super-fine sliding surfaces of ceramic material with which said plates lie against one another, said plates having essentially identical rectangular configuration with the ports of the stationary plates and the through-channels of the movable plate having the same pattern and the movable plate being movable along its longitudinal axis, the laminas forming the valve being arranged in a groove of a control valve block housing, the two outer laminas being held in the control block housing by a common retaining device which contains a retaining part having a pair of projections with each projections positively being engaged in notches in each of the stationary laminas to positively lock each lamina in position, said lamina forming the movable plate being mounted in a frame and held between said two laminas forming the stationary plates, and adjustment means for moving said movable plate along said sliding surfaces of the stationary plates between at least two positions with one of the two positions having the through-channels of the movable plate being aligned with the ports formed in the two stationary plates to enable flow therebetween and a second of the two positions having the through-channels of the movable plate out of alignment with the ports of the stationary plates to block flow of the agents, said adjustment means including a spring means for biasing the frame to said second position and dislocating means acting opposite to the direction of the spring means to move the frame and movable plate to the one position.

11. In a control valve means for a dental device for simultaneous control of a plurality of fluid agents for a dental instrument, said control valve means containing at least one valve, which is composed of a plurality of parts arranged on top of one another sandwich-like and forming a valve seat therebetween, an intake and discharge line for each of the plurality of agents as well as control lines under given conditions being connected to the valve, the improvements comprising the valve containing two stationary spaced plates with one plate having a plurality of ports with a separate port for each separate agent intake line and the other plate having a plurality of ports with a separate port for each separate discharge line extending to the instrument, and a movable plate having a longitudinal axis and forming a valve body adjustably arranged between the two stationary plates and having a through-channel proceeding at right angles to a plane of movement of the plate for each port in the one plate, each of said plates comprising a flat lamina completely composed of a ceramic material to provide super-fine sliding surfaces of ceramic material with which said plates lie against one another, said plates having essentially identical rectangular configuration with the ports of the stationary plates and the through-channels of the movable plate having the same pattern and the movable plate being movable along said longitudinal axis, the laminas of the valve being positioned between an upper housing part and a lower housing part, said upper housing part having a plate shape with a flat surface with intake channels in communication with the ports in the upper lamina of the valve and the lower housing part having a plate shape with a flat surface with discharge channels in communication with the ports in the lower stationary lamina, said upper and lower housing parts being releasably connected together and having resilient seals between the stationary lamina and the flat surface of the respective housing part, and adjustment means for moving said movable plate along said sliding surfaces of the stationary plates between at least two positions with one of the two positions having the through-channels of the movable plate being aligned with the ports formed in the two stationary plates to enable flow therebetween and to the instrument and a second of the two positions having the through-channels of the movable plate out of alignment with the ports of the stationary plates to block flow of the agents to the instrument.

12. In a control valve means according to claim 11, wherein a plurality of the valves are combined in a signal valve control block.

13. In a control valve means according to claim 12, wherein said control valve means has a common input control valve and a respective output control valve is provided for each instrument associated with the valve means.

14. In a control valve means according to claim 11, wherein said resilient seals bias the two stationary plates against the movable plate.

15. In a control valve means for a dental device for the simultaneous control of a plurality of fluid agents, said control valves means containing at least one valve, which is composed of a plurality of parts arranged on top of one another sandwich-like and forming the valve seat therebetween, an intake and discharge line for each of the plurality of agents as well as control lines under given conditions being connected to the valve, the improvements comprising said control valve means having a single valve control block having an output control valve for each instrument associated with the valve means and a common input control valve, each of said output control valves containing two stationary spaced plates with one plate having ports being connected to the agent intake lines and the other plate having ports being connected to the discharge lines, and a movable plate having a longitudinal axis, said movable plate forming a valve body adjustable arranged between the two stationary plates for movement along said longitudinal axis and having through-channels proceeding at right angles to a plane of movement, said plates being rectangular with flat, parallel surfaces comprising super-fine sliding surfaces of ceramic material with which the plates lie against one another, and adjustment means for moving said movable plate along said sliding surfaces of the stationary plates between at least two positions with one of the two positions having the through-channels of the movable plate being aligned with the ports formed in the two stationary plates to enable flow therebetween and a second of the two positions having the through-channels of the movable plate out of alignment with the ports of the stationary plates to block flow of the agents, said valve control block having an upper part and a lower part, said upper part having connections for the feed of agents to each connection for each of the output control valves for connecting a supply conduit thereto.

16. In a control valve means according to claim 15, which includes means biasing the sliding surfaces of the two stationary plates against the sliding surfaces of the movable plate.

17. In a control valve means for a dental service for the simultaneous control of a plurality of fluid agents to a dental instrument, said control valves means containing at least one valve, which is composed of a plurality of parts arranged on top of one another sandwich-like and forming a valve seat therebetween, an intake and discharge line for each of the plurality of agents as well as control lines under given conditions being connected to the valve, the improvements comprising the valve containing two stationary spaced flat plates with one plate having a plurality of ports with a separate port for each separate agent intake line and the other plate having a plurality of ports with a separate port for each separate discharge line extending to the dental instrument, and a movable flat plate having a longitudinal axis and forming a valve body adjustably arranged between the two stationary plates and having a through-channel proceeding at right angles to a plane of movement of the plate for each port in the one plate, each of said plates having a rectangular configuration and having superfine sliding surfaces of ceramic material with which said plates lie against one another, the movable plate being movable along its longitudinal axis, the plates of the valve being positioned between a plate-like upper housing part and a plate-like lower housing part, said upper housing part having intake channels in communication with the ports in the upper stationary plate of the valve and the lower housing part having discharge channels in communication with the ports in the lower stationary plate, said housing parts being releasably connected together and having resilient seal means between the stationary plates and their respective housing parts for sealing the ports and biasing the stationary plates against the movable plate, and adjustment means for moving said movable plate along said sliding surfaces of the stationary plates between at least two positions with one of the two positions having the through-channels of the movable plate being aligned with the ports formed in the two stationary plates to enable flow therebetween and to the instrument and a second of the two positions having the through-channels of the movable plate out of alignment with the ports of the stationary plates to block flow of the agents to the instrument.

* * * * *